United States Patent [19]

Revici

[11] Patent Number: 4,851,398
[45] Date of Patent: Jul. 25, 1989

[54] BISMUTH CONTAINING PHARMACEUTICAL COMPOSITIONS

[75] Inventor: Emanuel Revici, New York, N.Y.

[73] Assignee: Elena Avram, New York, N.Y.

[21] Appl. No.: 103,225

[22] Filed: Sep. 30, 1987

[51] Int. Cl.$^4$ ............................................... C11C 1/00
[52] U.S. Cl. ...................... 514/64; 514/496; 514/498; 514/503; 514/504; 514/560; 260/413
[58] Field of Search ................ 514/560, 64, 496, 498, 514/503, 504; 260/413 K, 413 L

[56] References Cited

U.S. PATENT DOCUMENTS

| | | | |
|---|---|---|---|
| 1,051,520 | 1/1913 | Schendler | 514/504 |
| 1,226,229 | 5/1917 | McLaughlin | 514/560 X |
| 1,547,165 | 7/1925 | Court et al. | 514/503 |
| 2,054,731 | 9/1936 | Pyman et al. | 514/503 |
| 2,769,006 | 10/1956 | Kalberg | 514/560 X |
| 3,321,367 | 5/1967 | Fuller et al. | 514/503 |
| 3,842,171 | 10/1974 | Friedham | 514/504 |
| 4,215,144 | 7/1980 | Thiele | 514/560 X |
| 4,642,317 | 2/1987 | Palmquist et al. | 514/560 X |
| 4,753,964 | 6/1988 | Horrobin | 514/558 |

FOREIGN PATENT DOCUMENTS

| | | | |
|---|---|---|---|
| 206487 | 5/1924 | United Kingdom | 514/503 |
| 455784 | 10/1936 | United Kingdom | 514/503 |
| 1011719 | 12/1965 | United Kingdom | 514/503 |

Primary Examiner—H. M. S. Sneed
Assistant Examiner—George R. Fourson
Attorney, Agent, or Firm—Pennie & Edmonds

[57] ABSTRACT

The invention relates to a method for making a composition which comprises selecting at least one fatty acid or fatty ester compound having an allylic unsaturation of the type —CH=CH—CH$_2$—CH=CH— or —CH=CH—CH=CH—CH$_2$—, adding to said compound a salt of an element having a rhombohedral crystal structure, such as Bi, Hg, As, B, Sb or Sm, to form a mixture, heating said mixture above about 260° C. for a sufficient period of time to incorporate at least about 0.1% by weight of the element into the compound, cooling the mixture, and recovering the incorporated compound as the remaining fluid of the mixture. The invention also relates to the reaction products thus produced along with methods of administering these compositions to a subject to treat abnormal conditions caused mainly by a catabolic imbalance.

13 Claims, No Drawings

BISMUTH CONTAINING PHARMACEUTICAL COMPOSITIONS

TECHNICAL FIELD

The present disclosure relates to anabolic agents of new lipidic compositions which have incorporated therein Bi or a similar element having a rhombohedral crystal structure, a method for preparing these compositions, and a method of use thereof to treat various conditions in a subject due mainly to a catabolic abnormality or imbalance.

SUMMARY OF THE INVENTION

The invention comprises novel compositions of lipidic materials, such as fatty acids, esters, or oils which include a group of elements having a rhombohedral crystal structure, such as Hg, Bi, As, Sb, B and Sm, incorporated therein. These compositions are made by heating the lipidic material to a temperature of at least about 260° C. for a sufficient time to incorporate a predetermined amount of the element into the oil. At least about 0.1% can be used, although amounts between about 0.5 and 10%, preferably about 5%, are preferred.

These compositions of the invention are anabolic or anti-catabolic agents and may be administered to a patient who has a catabolic imbalance as evidenced by symptoms of certain diseases or adverse effects, to correct such imbalance, to treat the symptoms of diseases or adverse effects caused by the imbalance, as well as to have an antiviral action.

DETAILED DESCRIPTION OF THE INVENTION

Inspite of the most intensive research efforts, practically little progress has been obtained in the treatment of most diseases, and especially in the treatment of AIDS—today the modern lethal plague. The following represents the basis for an approach important also for the results of its clinical applications.

My research has shown the capital importance of the recognition of different pathogenic occurrences with direct application for the therapeutic approach. I have thus shown the existence of a dualistic pathogenesis, anabolic—constructive or catabolic—destructive state which governs the biology in all its aspects. The normal state results from a dynamic balance between alternating anabolic and catabolic processes, while the abnormal state corresponds to imbalances due to the abnormal processes.

My new concept that the anabolic or catabolic character represents the fundamental aspect of a disease has put the problems of the pathological conditions from their pathogenesis to therapy entirely on a new basis.

Symptoms and analyses are serving to recognize the imbalance present and consequently to guide the choice and necessary amounts of appropriate agents to be administered. Fever, diarrhea, vomiting, nausea, perspiration, pain with an alkaline pattern, and insomnia represent the main symptoms of the catabolic imbalance. In blood analyses, the catabolic imbalance is evidenced by a high red cell sedimentation rate, eosinopenia, and leukopenia with high serum potassium. In the urinary system, characteristic analyses show a high oxyreduction potential, high specific gravity, low surface tension, low pH, and a low chloride excretion. The opposite symptoms and analyses correspond to an anabolic imbalance.

The further study of the cyto-histological changes have shown the anabolic imbalance to correspond to cells with manifest youth character, while the catabolic to correspond to old cells with pyknosis and kariorhetic changes. The study of these analyses has shown that while the oxyreduction is indicating a basic imbalance as related to the subnuclear level, other analyses, mainly the pH and the surface tension, are corresponding to superior level, and are consequently subject to more rapid and less general changes. While the oxyreduction provides information of a general more fixed basic imbalance, the pH and the surface tension are subject to more rapid and less basic changes. These considerations have special importance for the guided therapy.

Parallel to the recognition of the anabolic and catabolic imbalance, I studied the factors inducing them, to find the special role of the lipids. The study of the lipids in general has led to a new definition of these agents, as polar-nonpolar substances with the nonpolar group predominant. According to this research, the lipids represent the principal constituents, while the water-soluble fractions represent the secondary ones. The fact that the polar groups have electrostatic forces results in the existence of positively and negatively charged lipids. The most important positive lipids are the sterols, while the negative are the fatty acids.

It was found that the anabolic imbalances are directly related to the intervention of the lipids with positive polar groups, respectively, the sterols, while the catabolic imbalances result from the intervention of abnormal fatty acids, respectively, trienic conjugated compounds.

All the lipids of the body have their polar groups bound except for the brain and the red cells, which have free lipids. I have found that the lipids of the abnormal lesions are free, not combined, a fact which explains their special activity in the pathological conditions. As a direct consequence of this occurrence, I found that a lipid introduced in the body acts more directly upon the lesions.

I applied the dualistic concept for the study of the agents used therapeutically to find them to have either an anabolic or a catabolic character. I used an entire series of very concordant tests to determine this character. The study of the second day wound crust pH has shown a change toward more alkaline values for the agents with a catabolic action and more acid values for those with anabolic properties. The study of the curve of the surface of a healing wound has shown the presence of several peaks of the curve. An anabolic agent makes these peaks disappear, while a catabolic agent increases their value or numbers.

The study of the influence exerted by agents upon the oxygen intake by cancer cells or of yeast has shown a reduction of oxygen intake for the anabolic agents and an increase for the catabolic agents. The anabolic agents also induce a leukocytosis with eosinophilia, a lower sedimentation rate, a lower serum potassium, as well as marked urine analyses - such as higher surface tension, lower specific gravity and higher pH. The catabolic agents provide opposite changes, in these blood and urine analyses. In general, the alcohols and amines induce anabolic changes while the acids, aldehydes and ketones induce catabolic changes.

I have studied under this specific dualistic aspect many different elements, and have found several important characters. The members of the same series (i.e., those in vertical rows) of the periodic table have all been found to have the same anabolic or catabolic character. The members of the odd A series and of even B series are anabolic, while those of the A even and B odd series, catabolic.

The study of the periodic table has shown another important character. All the members of the same period, i.e., those in horizontal rows, are predilectly working at the same level of the organization, with the lowest periods at the more primary or basic level. The 6th period (starting with cesium) is thus acting predilectly to the lowest organizational level of the subnuclear entities. The elements of the 5th period (of rubidium) are acting predilectly upon the nuclear level, while those of the 4th period (of potassium) upon the cellular level. The elements of the 3rd period (of sodium) act upon the tissue and organ levels, while those of the second period (of lithium) upon the general systemic level.

It was this special systemization of the elements which has its main application in the study of their biological actions. Of special interest are the elements of the 6th period, which are acting predilectly at the subnuclear level.

I have also shown that different biological independent entities correspond to different levels of the organization. For example, the viruses are thus recognized as subnuclear entities, while the microbes as nuclear entities and not as cells as erroneously considered.

As a direct consequence, it was recognized that the elements of the 6th period would have special action upon the subnuclear level formations of the complex individual and at the same time on the viruses as being entities corresponding to this special level. It was under this aspect that these elements were further studied. Cs, Hb, W, Os, Pt, Hg, Tl and Bi are members of the subnuclear level and were found to be anabolic agents having anticatabolic properties.

I have applied other findings to this study of the elements. I have shown that there are the forces present in the atoms, which represent the factor which determine the kind of crystals they form. Elements forming the same kind of crystals, having similar forces, appear to have similar biological properties. By applying this view, I have found that, in general, from all the previously mentioned elements, only Hg, Bi, As, B, Sb and Sm have the same rhombohedral crystal form. In fact, all these rhombohedral elements, although of different series and periods have common biological properties: they are all anabolic. More importantly, the Hg, Bi, As and B have special antiseptic properties. Hg, Bi and As were the only elements which, for years, were used for the treatment of spirochetoses and more specifically, for treatment of syphilis. Also, As, Sb and Bi are members of the same very active anabolic series, the 6A. Furthermore, Bi represents also the anabolic element with the highest atomic weight, respectively acting at the lowest level of the organization. All these are making from the elements of the rhombohedral group of Bi, Hg, As, B, Sb and Sm, very highly interesting elements for special activities, such as antiviral and especially as anabolic agents at the lowest subnuclear level.

In the therapeutic study of these agents, I have found as a capital character that they should have lipidic properties, that is, to be more soluble in neutral organic solvents than in water. This allows the agents to be specifically taken up by the abnormal formation in the subject, which formation is rich in free lipids. The study of the activity of the different compounds of these important elements has shown the capital importance of this fundamental lipidic character. Some salts of the elements having a lipidic fatty acid component, such as, for example, oleate, palmitate, or the like, have not shown the desired effects. I explained this through the fact that the element as a cation in the compound is easily separated and bound to other nonlipidic anions. I resolved this problem by having the element directly incorporated into the nonpolar group of a lipidic substance. I made this especially by incorporating the element in the nonpolar part of the fatty acids at their double bonds.

In the following method, the element as such or in the form of a salt which is easily dissociated, is mixed with an oil or with its fatty acids or other unsaturated lipids, especially the polyunsaturated lipids. The mixture is heated to a temperature at which the dissociated element is attached to the lipid at their double bonds which, were previously bound to oxygen and which I found to open at this high temperature. The combination between the element and the double bond corresponds to an exothermic reaction. The heating is stopped at this moment with the result of the element incorporated in the nonpolar part of the fatty acids.

I have incorporated the elements of this rhombohedral group predilectly in vegetable oils such as sesame or safflower oil or its fatty acids. The problem of what compound has to be used has appeared capital for a good and sufficient incorporation of the element. The use of the element as such or other compounds has given insufficient results. I found that organic acid salts of these elements provide the best results. Thus, 5% by weight of bismuth oleate mixed with sesame oil is heated at around 300° C. under constant stirring for a sufficient time in order to obtain a good incorporation.

The allylically unsaturated compound is preferably a naturally occurring oil containing polyunsaturated fatty ester, such as an animal, vegetable, or fish oil, and, particularly, polyunsaturated vegetable oils. Sesame oil, a vegetable oil consisting largely of triglycerides, is the most advantageous composition found to date in the practice of this invention.

The composition utilized should contain a significant percentage of molecular species having allylic moieties to render the compositions useful according to the invention. Such moieties are indicated by the following partial structures $-CH=CH-CH_2-CH=CH-$ and /or $-CH=CH-CH=CH-CH_2-$. As indicated, the unsaturation can be conjugated or nonconjugated, but the composition must contain allylic methylene hydrogen.

Such compositions may initially be oxidized or heated in the presence of air or oxygen at the temperature range between about 100 and about 150° C. The oxygen can be obtained by merely heating the composition in a vessel which is open to the atmosphere, but preferably and advantageously, the source of oxygen is a gas such as air which is injected into the heated oil. Introduction of air also provides a source of agitation.

The heating step is conducted for a period of from about 15 minutes to about three hours. The temperature should be maintained at an upper limit within the range of above about 260° to 325° C. and preferably about 280° to 300° C. These temperature limitations are based on a heating time of about one-half hour. The temperatures can be altered within limits depending on the time of heating. For example, when the temperature is about 265° C., the time is about one-half hour, while temperature as high as 300° C. require a shorter period of time for heating. Higher temperatures for a prolonged period of time tend to degrade the composition and should thus be avoided.

Agitation, by stirring for example, aids in the reaction, and experiments to date indicate that a fairly vigorous stirring is advantageous. The introduction of air into the mixture during the heating is also very advantageous, particularly when the mixture is not subjected to prolonged heating and thus, is the preferred method. The mixing or stirring can be accomplished with the introduction of the air. After the reaction has taken place, the mixture is cooled. The remaining fluid is ready for use after appropriate sterilization for injection or incorporated into capsules, such as gelatin, for oral administration.

The precise nature of the compositions which result from the above-described treatment or the identity of the effective component or components is not presently known. It is known, however, that these compositions do include the range of about 0.1 to 10% weight percent has been found to be effective.

As mentioned above, although any organic salt can be used, including carbonate, acetate, or the like with the element bonding the fatty acids present in the oil. Although any amount above 0.1% of the element incorporated into the composition is useful, the preferred amount ranges between about 0.5 to 10, and most preferably about 5, weight percent.

The so obtained incorporated product is used for oral administration, and after sterilization, for intramuscular injections. The incorporated element have a very low toxicity with no undesired side effects. A certain pharmacological activity is found in all the compounds of the rhombohedral elements in general. More accentuated are their lipidic compounds. Especially active, however, are the bismuth and mercury compounds incorporated alone or in combination in oils, in their fatty acids or in other different agents with lipidic properties.

In the pharmacological activity of lipidic rhombohedral elements and especially of the incorporated bismuth or mercury, several actions are recognized. In one, the anabolic bismuth or mercury lipidic compound acts again the catabolic imbalance present as such, that is, reducing or even fully controlling this imbalance. This is very manifest for severe pain, controlled in less than an hour, by an oral intake of very small amounts of the incorporated bismuth or mercury compound, such as corresponding to 0.2–0.5 mg per dose. For intramuscular injection, a preferred daily dosage of between 0.5 to 10 cc per dose, administered once or twice daily, has been found to be generally effective, although additional doses could be administered for extreme situations. As such, the incorporated rhombohedral elements are working on many different conditions.

These analyses and clinical manifestations have to be changed by the administration of the incorporated compound. In a 5% preparation, amounts from about 0.5 to 10 cc daily are predilectly used for the treatment of catabolic imbalance. Other concentrations of agents can be converted to other doses containing the same or similar amount of active ingredient (i.e., the incorporated compound). In general, the higher the dose used, the better are the clinical results.

Bismuth and the other elements of the group incorporated act thus upon other catabolic symptoms. Frank are the changes in the subjective manifestations of the neoplastic diseases, especially pain, difficulties in breathing and others. This applies also to the clinical manifestations of AIDS with characteristic catabolic imbalances, which manifestations are often fully controlled in a short time.

In another action, especially with higher doses the anabolic compounds and especially the bismuth or mercury incorporated compounds are inducing by themselves an anabolic imbalance. As this imbalance is not sterolic, it does not have the noxious effects of the usual sterolic imbalances. I have found that the presence of a nonsterolic anabolic imbalance is reducing the amount of sterols in the body. This is especially important for the neoplastic lesions, which are in general developing only with a sterolic imbalance. Consequently, especially the incorporated bismuth or mercury have through the nonsterolic anabolic exaggerated imbalance a special action also upon the anabolic lesions of the neoplastic diseases as well as other conditions. The direct anticatabolic action and the special exaggerated anabolic nonsterolic imbalance induced are leading to the destruction of such neoplastic lesions. Such organic changes were seen also in other conditions. Large lymphatic glands and the Kaposi lesions in AIDS have been reduced even after relatively a short treatment.

Another very important action is this of Bi and Hg, due to the fact that they are part of the elements of the 6th period, elements acting predominantly upon the subnuclear level. They act especially also upon the independent entities corresponding to this level, i.e., the viruses. With a treatment for some longer time and insufficiently high doses, it is expected to obtain a control of such viral diseases.

It was found that the treatment with incorporated rhombohedral elements has to be continued for sufficient time in adequate high amounts in order to obtain the desired results, i.e., other than the very impressive immediate effects on pain and other symptoms more especially.

Bismuth, mercury or arsenic can be used also in the different preparations, which were used especially for the treatment of syphilis. These agents of incorporated rhombohedral elements are used successfully together with other different agents, especially with those having anabolic properties, to enhance their anticatabolic action. They are also used with active catabolic agents, together or following their administration, in order to control exaggerated anabolic manifestations.

There are these different actions which are explaining the favorable effects obtained with the incorporated rhombohedral elements in a variety of pathological conditions, especially cancer, leukemias and viral conditions, mainly AIDS, herpes and Epstein-Barr disease.

There are these results already obtained and especially the multiple successful applications, which are making from the lipidic rhombohedral elements compounds in general and especially from the incorporated bismuth or mercury special valuable weapons in the fight against different diseases.

While it is apparent that the invention herein disclosed is well calculated to fulfill the objects above stated, it will be appreciated that numerous modifications and embodiments may be devised by those skilled in the art, and it is intended that the append claims cover all such modifications and embodiments as fall within the true spirit and scope of the present invention.

What is claimed is:

1. A method for making a composition which comprises:

selecting at least one fatty acid or fatty ester compound having an allylic unsaturation of the type —CH=CH—CH$_2$—CH=CH— or —CH=CH—CH=CH—CH$_2$—;

adding to said compound at least one element having a rhombohedral crystal structure or a salt of said at least one element, said salt being substantially non-reactive with the compound at room temperature to form a mixture;

heating said mixture above about 260° C. for a sufficient period of time to form a composition having at least about 0.1% by weight of the element incorporated in said composition;

cooling the mixture; and recovering the composition as the remaining fluid of the mixture.

2. The method of claim 1 wherein the fatty acid or fatty ester compound is initially oxidized by mixing the compound with air and heating the mixture.

3. The method of claim 1 wherein the mixture is heated at a temperature range of about 160° C. to 325° C. for a time of at least about one-half hour so as to incorporate at least 1% by weight of the at least one element into the composition.

4. The method of claim 1 wherein the element is either Bi, Hg, Sm, As, B, Sb or mixtures thereof.

5. The method of claim 1 wherein the unsaturated compound is a vegetable oil.

6. A method for making a composition which comprises:

selecting at least one fatty acid or fatty ester compound having an allylic unsaturation of the type —CH=CH—CH$_2$—CH=CH— or —CH=CH—CH=CH—CH$_2$—;

adding to said compound an element selected from the group consisting of Bi, Hg, As, B, Sm, Sb, and combinations thereof, or a salt of said element, said salt being substantially non-reactive with the compound at room temperature to form a mixture;

heating said mixture above about 160° C. for a sufficient period of time to form a composition having at least about 0.1% by weight of the element incorporated in said composition;

cooling the mixture; and recovering the composition as the remaining fluid of the mixture.

7. The method of claim 6 wherein the unsaturated compound is a vegetable oil.

8. The composition produced by the method of claim 1.

9. The composition produced by the method of claim 6.

10. A method for treating a subject suffering subjective manifestations of abnormal conditions caused by a catabolic imbalance due to AIDS without treating the conditions which comprises administering to said subject a therapeutically effective amount of an anticatabolic agent comprising the composition according to claim 8.

11. A method for treating a subject suffering subjective manifestations abnormal conditions caused by a catabolic imbalance due to AIDS without treating the conditions which comprises administering to said subject a therapeutically effective amount of an anticatabolic agent comprising the composition according to claim 9.

12. The method of claim 10 wherein about 0.5 to 10 cc of the agent is administered daily to the subject.

13. The method of claim 11 wherein about 0.5 to 10 cc of the agent is administered daily to the subject.

* * * * *